United States Patent
Krstic et al.

(10) Patent No.: US 8,183,648 B2
(45) Date of Patent: May 22, 2012

(54) NANOSCOPIC ELECTRODE MOLECULAR PROBES

(75) Inventors: Predrag S. Krstic, Knoxville, TN (US); Vincent Meunier, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 440 days.

(21) Appl. No.: 12/321,823

(22) Filed: Jan. 26, 2009

(65) Prior Publication Data

US 2009/0295372 A1 Dec. 3, 2009

Related U.S. Application Data

(60) Provisional application No. 61/062,480, filed on Jan. 25, 2008.

(51) Int. Cl.
*H01L 51/00* (2006.01)
*C12Q 1/68* (2006.01)
*G01N 27/403* (2006.01)

(52) U.S. Cl. ............... 257/414; 257/E51.045; 435/6.1; 438/1; 977/748; 977/848; 977/941; 977/946

(58) Field of Classification Search .............. 257/40, 257/E51.001–E51.052, 414; 438/99, 1; 977/745–746, 748, 840, 848, 941, 943–946, 977/953, 957–958; 435/6.1
See application file for complete search history.

(56) References Cited

U.S. PATENT DOCUMENTS

| | | | |
|---|---|---|---|
| 6,187,823 B1 * | 2/2001 | Haddon et al. | 516/32 |
| 2005/0126913 A1 * | 6/2005 | Burke et al. | 204/547 |
| 2008/0017845 A1 * | 1/2008 | Drndic et al. | 257/24 |
| 2008/0035913 A1 * | 2/2008 | Lake et al. | 257/40 |
| 2008/0171316 A1 * | 7/2008 | Golovchenko et al. | 435/6 |

OTHER PUBLICATIONS

Wang, X., et al. "Carbon Nanotube-DNA Nanoarchitectures and Electronic Functionality." Small, vol. 2 (2006): pp. 1356-1365.*
Singh, K.V., et al. "Covalent Functionalization of Single Walled Carbon Nanotubes with Peptide Nucleic Acid: Nanocomponents for Molecular Level Electronics." Carbon, vol. 44 (2006): pp. 1730-1739.*
Pandey, R.R., et al. "Carbon Nanotube-Molecular Resonant Tunneling Diode." Phys. Stat. Sol. (A), vol. 203 (2006): pp. R5-R7.*
Guo, X., et al. "Covalently Bridging Gaps in Single-Walled Carbon Nanotubes with Conducting Molecules." Science, vol. 311 (2006): pp. 356-359.*
Feuntes-Cabrerra, M., et al. "Benzo-Homologated Nucleobases in a Nanotube-Electrode Set-Up for DNA Sequencing." Nanotech., vol. 18 (2007): pp. 1-4.*
Bruque, N.A. et al. "Self-Assembled Carbon Nanotubes for Electronic Circuit and Device Applications." J. Nanoelectron. Optoelectron., vol. 1 (2006): pp. 74-81.*
Li, J., et al. "Carbon Nanotube Nanoelectrode Array for Ultrasensitive DNA Detection." Nanolett., vol. 3, No. 5 (2003): pp. 597-602.*

(Continued)

*Primary Examiner* — Matthew W Such
(74) *Attorney, Agent, or Firm* — Scully, Scott, Murphy & Presser, P.C.

(57) ABSTRACT

The present invention relates to a method and apparatus for enhancing the electron transport property measurements of a molecule when the molecule is placed between chemically functionalized carbon-based nanoscopic electrodes to which a suitable voltage bias is applied. The invention includes selecting a dopant atom for the nanoscopic electrodes, the dopant atoms being chemically similar to atoms present in the molecule, and functionalizing the outer surface and terminations of the electrodes with the dopant atoms.

43 Claims, 3 Drawing Sheets
(3 of 3 Drawing Sheet(s) Filed in Color)

OTHER PUBLICATIONS

Ewels C.P. et al., "Nitrogen Doping in Carbon Nanotubes", *Journal of Nanoscience and Nanotechnology* 5(9):1345-1363 (2005).

Roy S. et al., "Direct Electrical Measurements on Single-Molecule Genomic DNA Using Single-Walled Carbon Nanotubes", *Nano Letters* 8(1):26-30 (2008).

He J. et al., "Transverse Tunneling Through DNA Hydrogen Bonded to an Electrode", *Nano Letters* 8(8):2530-2534 (2008).

Tuukkanen S. et al., "Carbon Nanotubes as Electrodes for Dielectrophoresis of DNA", *Nano Letters* 6(7):1339-1343 (2006).

Krstic V. et al., "Nitrogen Doping of Metallic Single-Walled Carbon Nanotubes: N-Type Conduction and Dipole Scattering", *A Letters Journal of Exploring the Frontiers of Physics* 77:37001-p1-37001-p5 (2007).

Meunier V. et al., "Enhancement of the Transverse Conductance in DNA Nucleotides", *The Journal of Chemical Physics* 128:041103-1-041103-4 (2008).

Sumpter B.G. et al., "Nitrogen-Mediated Carbon Nanotube Growth: Diameter Reduction, Metallicity, Bundle Dispersability, and Bamboo-Like Structure Formation", *American Chemical Society* 1(4):369-375 (2007).

Wong S.S. et al., "Covalently Functionalized Nanotubes as Nanometre-Sized Probes in Chemistry and Biology", *Nature* 394:52-55 (1998).

Majumder M. et al., "Effect of Tip Functionalization on Transport Through Vertically Oriented Carbon Nanotube Membranes", *J. American Chemical Society* 127:9062-9070 (2005).

Bernholc J. et al., "Mechanical and Electrical Properties of Nanotubes", *Annu. Rev. Mater. Res.* 32:347-375 (2002).

Shimotani K. et al., "An Advanced Electric Probing System: Measuring DNA Derivatives", *Journal of Chemical Physics* 118(17):8016-8022 (2003).

Liu K. et al., "Electrical Transport in Doped Multiwalled Carbon Nanotubes", *Physical Review B* 63:161404-1-161404-4 (2001).

Rochefort A., "Electron Interference Effects on the Conductance of Doped Carbon Nanotubes", *The Journal of Physical Chemistry* 104(44):9807-9811 (2000).

Latil S. et al., "Mesoscopic Transport in Chemically Doped Carbon Nanotubes", *Physical Review Letters* 92(25):256805-1-256805-4 (2004).

Maldonado S., "Preparation and Characterization of Nitrogen Doped Carbon Nanotube Electrode Materials", *Dissertation The University of Texas at Austin* 1-189 (2006).

* cited by examiner

NANOSCOPIC ELECTRODE MOLECULAR PROBES

This application is relates to and claims the benefit of U.S. Provisional Patent Application Ser. No. 61/062,480 filed Jan. 25, 2008, the entire contents and disclosure of which is incorporated by reference herein.

This invention was made with government support under Contract Number DE-AC05-00OR22725 between the United States Department of Energy and UT-Battelle, LLC, and under contract number 1 R21 HG003578-01 by the U.S. National Human Genome Research Institute of the National Institutes of Health. The U.S. government has certain rights in this invention.

FIELD OF THE INVENTION

The present invention relates to methods and an apparatus for probing the electronic properties of molecules, and more particularly, to methods and apparatus for molecular sensing and identification.

BACKGROUND OF THE INVENTION

The possibility of genome sequencing by measuring the transverse conductivity upon applied DC bias while a DNA strand is translocated through a nanogap or nanopore has recently been the subject of debate based on theoretical considerations and experimental results. See, for example, R. Zikic et al, Phys. Rev. E 74, 011919 (2006); J. Lagerqvist et al, Nano Lett. 6, 779 (2006); M. Zwolak, and M. Di Ventra, Nano Letters 5, 421 (2005); and M. Zwolak, and M. Di Ventra, arXiv, cond-mat/0708.2724v1). The origin of the debate stems from the fact that the Fermi energy of gold electrodes at 0K is rather far (~2 eV) from the molecular eigen-levels of the DNA nucleotides. The electronic transport is therefore dominated by non-resonant tunneling, which is highly dependent on the difficult-to-control relative geometry between the molecule and electrodes, while it is weakly dependent on the electronic structure of the molecule.

In addition, the geometry between the molecule-electrodes complex is influenced by aqueous and electrolytic environment, thermal phenomena, and the effects of the applied transverse as well as longitudinal (translocating) electric fields. With a low transverse voltage bias and picoampere (pA) and sub-pA tunneling currents, the main difficulty remains in the poor signal-to-noise ratio, which weakens the predictive power of distinguishing various nucleotides, or even detecting their presence. These uncertainties are the subject of recent controversy in the literature. See, for example, J. Lagerqvist et al, Phys. Rev. E, 76, 3 (2007) and R. Zikic et al., Phys. Rev. E 76, 2 (2007). Higher bias is unacceptable in an actual device realization. Besides other possible destructive and nonlinear effects, electric forces at the negatively charged backbone of a DNA molecule move the molecule toward the anode, thereby disabling the translocation.

Conductance measurements are most commonly performed using standard metallic probes, such as gold, See, for example, M. A. Reed et al., Science 278, 252 (1997). Unfortunately, when DNA segments are sandwiched between this type of large cross-section electrodes, the structural deformations at the interface between electrodes and the base pairs can cause unacceptable variations in the measured current. See, for example, K. Tagami et al., Jap. J. of App. Phys. 42, 5887 (2003) and K. Tagami, L. G. Wang, and M. Tsukada, Nano Letters 4, 209 (2004).

The interface sensitivity in quantum transport is not only limited to measuring the current across DNA, it is a universal effect that makes measurement in single molecules particularly difficult. For that reason, there is currently a strong interest in the development of an experimental apparatus that will alleviate the difficulty of controlling the coupling between the electrodes and the molecules. One attractive idea is to develop a system where the coupling between the molecule and the electrodes is better localized, in such a way as to ensure higher reproducibility of measured current-voltage curves.

For instance, advanced two-probe electric systems have been devised to measure geometrical and electronic properties of DNA and DNA derivatives. See, for example, K. Shimotani et al., J. of Chem. Phys. 118, 8016 (2003). In this device, the tip is replaced by a carbon nanotube in order to probe nanometer-scale samples, since the probe must have a radius of curvature smaller than the size of the samples.

Since carbon nanotubes (CNTs) were discovered in 1990 (S. Iijima, Nature 354, 56 (1991), intense research into their applications in various fields of materials science continues at a rapid pace. See, for example, J. Bernholc et al., Ann. Rev. of Mat. Res. 32, 347 (2002). One active area of research has been the application of CNT tips as precision nanotools for manipulating biological molecules. Such research has been primarily directed to deciphering the relationship between structure and function in molecules. CNT tips are of particular interest due, in part, to their high aspect ratio that allows for imaging with higher spatial resolution. See, for example, L. Q. Quo et al., Physica E, 27, 240 (2005) and L. Q. Quo et al., App. Surf. Sc. 228, 53 (2004).

The appeal of carbon nanotubes does not only stem from their unique morphology but also because their terminal ends can be conveniently functionalized by chemical modification. See, for example, M. Majumder, N. Chopra, and B. J. Hinds, J. Am. Chem. Soc. 127, 9062 (2005) and S. S. Wong et al., Nature 394, 52 (1998). End doping can be done during growth as long as the dopant has a surfactant behavior. Functionalization has been used, for example, to improve desired properties, such as increased coupling or decreased work function for field emission purposes. See, for example, J. C. Charlier et al., Nano Letters 2, 1191 (2002); V. Meunier et al., App. Phys. Lett. 81, 46 (2002), and A. Maiti et al. Phys. Rev. Lett. 87, 155502 (2001).

A CNT has also been used as an electrode for dielectrophoretic trapping of DNA molecules as a way for achieving a high enough field gradient for trapping purposes while using low trapping voltages. See, for example, S. Tuukkanen et al., Nano Letters 6, 1339 (2006). Single DNA chains have also been chemically grafted onto aligned CNT electrodes as part of an effort to develop DNA-CNT sensors of high sensitivity and selectivity. See, for example, P. G. He, and L. M. Dai, Chem. Comm., 3, 348 (2004).

Previous experimental achievements, like those cited above, typically involve covalent bonding between the CNT tip and the molecule of interest. However, covalent binding of the molecule to the electrode can be problematic if a process is to be performed on the molecule that requires its freedom of movement. For example, covalent binding of DNA to the electrode would not be permissible in an application wherein a conductivity measurement is also used as a sequencing method. In such an application, the DNA strand would need to have the freedom to be easily threaded inside a nanogap created between the nanotube electrodes.

There remains a need in the art for measuring the electron transport properties of molecules with greater precision. A method that could achieve this would provide several benefits including, for example, the ability to identify a molecule or distinguish one molecule from another.

SUMMARY OF THE INVENTION

The present invention advantageously provides means for enhancing electron transport measurements of a molecule that is positioned between nanoscopic electrodes for study. The invention achieves this by choosing dopant atoms in conductive carbon-based nanoscopic electrodes in a selective manner whereby the dopant atoms are chemically similar to non-carbon, non-hydrogen (non-C,H) atoms present in the molecule.

The selective doping is believed to provide better matching of the Fermi energy of the electrode and the energy levels of the molecule (coupled to the electrodes, with either weak, non-covalent or strong covalent coupling) so that a resonant or quasi-resonant tunneling mechanism is realized during electron transport through the molecule. The quasi-resonant or resonant tunneling mechanism facilitates the transmission of much larger currents through the molecule as compared to the non-resonant tunneling mechanisms relied upon in the prior art.

An enhanced current response permits more sensitive detection and identification of a molecule of interest relative to other molecules, i.e., greatly improved signal-to-noise ratio in detecting a molecule of interest. Therefore, the present invention provides methods and an apparatus useful for, inter alia, making molecular sensors and probes.

In one embodiment, the invention provides a method for enhancing the electron transport properties of a molecule when the molecule is placed in the nanogap between carbon-based nanoscopic electrodes to which a suitable voltage bias is applied. The method is achieved by using an electrode having doped thereon a non-carbon main group dopant atom which is chemically similar to non-C,H atoms present in the molecule. By selecting the dopant atoms of the nanoscopic electrodes to be chemically similar to non-C,H atoms present in the molecule, enhanced electron transport selectivity is made possible for the molecule being studied.

In another embodiment, the invention provides a method for enhancing the electron transport property measurement of a molecule when the molecule is positioned between carbon-based nanoscopic electrodes to which a low voltage bias is applied, by selecting a non-carbon main group dopant atom that is chemically similar to non-C,H atoms present in the molecule, and functionalizing the outer surface of the electrodes with the selected dopant atoms.

In still another embodiment, the invention provides a method for enhancing an electron transport property measurement of a molecule being studied, by selecting a carbon-based nanoscopic electrode having non-carbon dopant atoms thereon that are chemically similar to non-C,H atoms present in the molecule, and measuring the electron transport property of the molecule when the molecule is positioned between carbon-based nanoscopic electrodes to which a low voltage bias is applied.

In yet another embodiment, the invention is directed to a method providing the steps of (i) positioning a molecule of interest within a nanosized gap separating at least two electrically conductive carbon-based nanoscopic electrodes in such a manner that the molecule bridges and interacts with the nanoscopic electrodes, wherein the nanosized gap is suitably miniscule so as to permit transmission of current through the bridging molecule by a tunneling mechanism while large enough to accommodate the molecule of interest; (ii) applying a voltage bias to the nanoscopic electrodes where the voltage bias is of a suitable magnitude so as to permit transmission of current by a tunneling mechanism; and (iii) measuring an electronic property (e.g., an electron transport property) of the bridging molecule. The nanoscopic electrodes are outer-surface functionalized by one or more non-carbon main group dopant atoms residing in a location of the nanoscopic electrodes atomically close to the nanosized gap, preferably terminating the electrode. In addition, the dopant atoms in the nanoscopic electrodes are preferably selected to be chemically similar to non-C,H atoms located in the molecule of interest, thereby providing an enhanced and more localized coupling between the molecule and doped electrodes.

Although this application focuses on carbon-based nanoscopic electrodes, it is important to realize that the invention is not necessarily limited to this particular class of electrodes. The principles and features described herein can also be appropriately applied to several other types of conductive electrodes, including, for example, those metallic types of electrodes which can be chemically functionalized.

The invention advantageously provides a significant enhancement of transmitted current at low bias, thereby overcoming many of the shortcomings of the prior art. A particular advantage of the invention is that the measurement enhancements described above can be realized for any molecule of interest by selecting dopant atoms in the nanoscopic electrodes that are chemically similar to non-C,H atoms found in the molecule.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
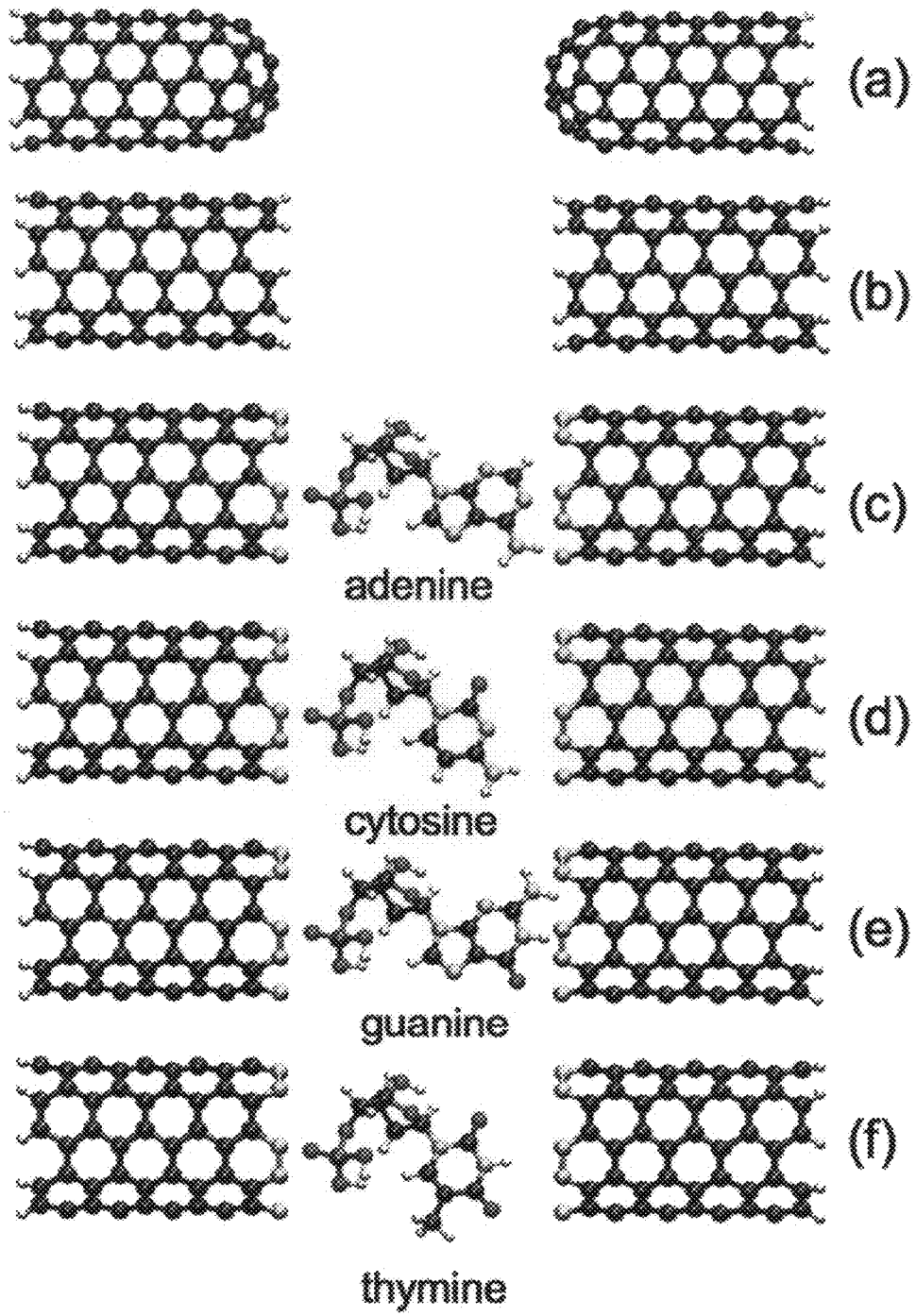
FIG. 1. (color) Configurations of the CNT leads and molecules for the calculation of electronic transmission, (a) and (b): Empty nanogap between carbon-capped and H-terminated CNTs. (c-f): Detailed structure of nanogap created between N-terminated CNT with nucleotides, as shown explicitly for adenine, cytosine, guanine, and thymine, respectively. In each case, the DNA bases include a sugar-phosphate group. The distance between the CNT tips was kept at 1.5 nm. In this figure, all lead layers of the extended molecule used in the calculation are shown. Nitrogen, carbon, hydrogen, oxygen, and phosphorus atoms are shown in yellow, blue, white, red, and gold.

The present invention provides enhanced measurement of the electron transport across a molecule when the molecule is positioned between carbon-based, chemically functionalized nanoscopic electrodes to which a suitable voltage bias is applied.

The electron transport property to be measured of the bridging molecule is any response from the molecule that can arise by application of a suitable voltage bias to the molecule. Typically, the electron transport property being measured is transverse tunneling current. Transverse tunneling current can in turn be used as a measure of the conductivity for the molecule. For example, in a preferred embodiment, the transverse tunneling current of DNA can be measured by attaching suitably doped carbon nanotube (CNT) electrodes to macroscopic electrode pads, positioning the DNA to bridge between the CNT electrodes separated by a suitably sized nanogap, and observing the current that tunnels from one electrode through the DNA to the other electrode. The techniques used for measuring a voltage-induced response in the molecule can be any of the standard techniques used for measuring the transport properties of nanoscale devices (such as CNT FETs or similar devices known in the art that use nanowires or nanoparticles as active elements).

The method enhances electron transport by increasing the resonant tunneling contribution which in turn increases the magnitude of the transverse tunneling current. For example, whereas the undoped CNTs have demonstrated tunneling currents in the range of picoamperes (pA), the present invention is capable of achieving tunneling currents through molecules in the nanoampere (nA) range.

The molecule to be studied can be essentially any molecule, but more suitably the molecule to be studied is an organic molecule which includes at least one non-carbon non-hydrogen (non-C,H) atom. More suitably, the non-C,H atom is selected from the main group elements. As used herein, the "main group elements" refer to the group of elements that include any of the Group IIIA (boron group), Group VA (nitrogen group), Group VIA (oxygen group), and Group VIIA (halogen group) elements.

In one embodiment, the molecule being studied is a biomolecule. A biomolecule is any molecule that is involved in a biological process or found in a living organism. Non-C,H atoms in most biomolecules are typically limited to nitrogen (N), oxygen (O), phosphorus (P), and sulfur (S).

The biomolecule can be, for example, a nucleobase-containing molecule. Some examples of nucleobases include the pyrimidines (e.g., cytosine, thymine, and uracil) and the purines (e.g., adenine and guanine). Some examples of nucleobase-containing molecules that can be studied herein include the nucleobases themselves, their closely related analogs and derivatives, as well as nucleosides, nucleotides, oligonucleotides, and nucleic acid polymers. The oligonucleotides and nucleic acid polymers can be deoxyribonucleic acid (DNA)-based or ribonucleic acid (RNA)-based.

The biomolecule can also be, for example, an amino acid-containing molecule. Some examples of amino acid-containing molecules include the amino acids, peptides, oligopeptides, and polypeptides (e.g., proteins, such as enzymes). Other types of biomolecules that can studied according to the invention include, for example, carbohydrates, lipids, neurotransmitters, and hormones.

In other embodiments, the molecule of interest may be, for example, an explosive, a harmful chemical (e.g., carcinogen or nerve agent), an environmental contaminant or pollutant, or a synthetic material for which analysis is required.

The method uses a nanoscopic electrode system for interacting with, and measuring the electron transport properties of, a molecule of interest. By "nanoscopic" is meant that the electrodes are of nanoscale dimensions (nanosized), i.e., a dimension sufficiently small that the properties of an object of such dimensions are predominantly governed by the behavior of individual atoms. Typically, a nanoscopic or nanoscale object refers to an object having at least one dimension within a range of about 1 to 100 nanometers (nm).

The nanoscopic electrode system includes at least two electrically conductive carbon-based nanoscopic electrodes separated by a nanosized gap (nanogap). When a molecule of interest is to be studied, the molecule is positioned within the nanosized gap in such a manner that the molecule bridges and interacts with the electrodes. The molecule can be positioned spontaneously (electrodes embedded into an environment containing the molecule) or by any suitable method known in the art, such as, for example, by controlled manipulation using dielectrophoresis (DEP).

The interaction between the molecule and electrodes can be any suitable interaction, including all of the known bonding and interaction modes that can occur between atoms or molecules. Some examples of bonding modes include covalent, hydrogen bonding, and ionic bonding. Some examples of nonbonding interaction modes include van der Waals, London dispersion, and dative interactions.

Preferably, the interaction between the molecule and electrodes is a non-covalent weak coupling interaction that confers a high degree of freedom of movement (i.e., low level of constraint) to the molecule. By this weak coupling interaction, the molecule may also be reversibly removed from the electrode system (or repositioned therein) without causing the breaking of bonds. The molecule-electrode interaction is of a degree similar to a van der Waals or London dispersion interaction.

Covalent bonding of the molecule may not be preferable when the electrodes are intended to be reused. The reason is that covalent bonding chemically alters the electrodes, thus rendering them unusable for future use in observing other molecules. However, covalent bonding may be acceptable where the electrode devices are intended to be for one-time use (e.g., discardable, or at least not re-applicable or reusable).

The nanogap is suitably miniscule in size so as to permit transmission of current by a tunneling mechanism. In order to accommodate a molecule of interest, the nanogap must also be at least as large as the bridging dimension of the molecule that bridges the electrodes. For the purpose of measuring electron transport properties of nucleobases, nucleosides, or nucleotides, the nanogap is preferably in the range of about 1 nm to 3 nm, more preferably between 1 to 2 nm.

The nanosized gap can be constructed by any of the means known in the art. For example, the nanogap can be an incision of desired dimension in a nanotube (CNT) connected to external electrodes. The external electrodes can be connected to contact pads that are in communication with external devices useful for data collection. The nanotube can be cut according to any of the known methods, including by lithographic means or running a brief pulse of current of suitable magnitude through the carbon nanotube. In the latter case, the size of the gap is roughly determined by the magnitude of the current pulse used. The nanogap can also be, for example, produced from a metal using similar methods described above.

Once the molecule is properly positioned, a voltage bias (preferably a low voltage bias) is applied to the bridging molecule through the nanoscopic electrodes. The applied voltage can be any suitable voltage which provides a tunneling current through the bridging molecule in the nanogap without causing destructive or disabling effects on the bridging molecule or nanoscopic electrodes. For example, in most applications a voltage bias of about 0.05 to about 1.0V is suitable. More preferable is a voltage of about 0.1 to about 0.6V (e.g., a voltage of about 0.4V).

The nanoscopic electrodes are, at least to some degree, electrically conductive. The nanoscopic electrodes are electrically conductive in that they can transmit an electrical current. For example, the nanoscopic electrodes can be semiconductors, conductors, or superconductors.

The nanoscopic electrodes are preferably carbon-based. In one embodiment, the nanoscopic electrodes are composed solely of carbon. In another embodiment, the electrodes are composed of carbon (and optionally hydrogen) and an additional one or more elements other than carbon and hydrogen. In another embodiment, the nanoscopic electrodes are composed of only carbon and hydrogen (i.e., hydrocarbon materials).

Typically, electrically conductive carbon-based materials are unsaturated, and more typically, are unsaturated by containing conjugated $sp^2$-hybridized carbon atoms engaged in carbon-carbon double bonds. Some examples of conductive carbon-based materials include graphite, fillerenes, carbon nanotubes, carbon nanobuds, carbon nanohoms, and their combined forms. The carbon-based materials can be of any suitable shape, including open or enclosed. Open carbon-based materials can be, for example, curved, flat, or twisted, and do not typically possess distinguishable inner and outer surfaces. However, an enclosed carbon-based material, such as a carbon nanotube or fullerene, has an inner (enclosed and typically inaccessible) surface which is distinguishable from an outer (exposed and typically accessible) surface.

For the purposes of this invention, the conductive nanoscopic electrodes described above have been outer-surface functionalized by one or more non-carbon main group dopant atoms. The nanoscopic electrodes are outer-surface functionalized by having dopant atoms residing on a location of the electrode which is accessible to the molecule of interest and the nanogap. For enclosed types of nanoscopic electrodes (e.g., carbon nanotubes or fillerenes), the dopant atoms are made accessible by having them reside on the outer surface as opposed to the inner surface.

In a preferred embodiment, the nanoscopic electrodes are carbon nanotubes. As known in the art, carbon nanotubes are enclosed and tubular in shape. They are typically only a few nanometers in diameter and can have variable lengths of anywhere between nanometers to millimeters. The carbon nanotube can be any of the types of carbon nanotubes known in the art, including, for example, a single-walled carbon nanotube (SWNT), double-walled carbon nanotube (DWNT), or multiwalled carbon nanotube (MWNT). A single-walled carbon nanotube can have any suitable conformation, such as, for example, a zig zag mode (where m=0 of a n,m chiral vector), armchair mode (n=m), or chiral mode (all other chiral vector combinations). Preferably, the nanotube is metallic, i.e., n-m is a multiple of 3.

The synthesis of carbon nanotubes is well known in the art, and includes such methods as arc discharge, laser ablation, and chemical vapor deposition (CVD). Of these, CVD is the simplest and most widespread method. CVD also provides the advantage of being the most versatile growth method for introducing dopant atoms into the carbon network. An implementation of CVD in a molecular beam environment (MBE) provides a highly controlled method similar to the manner in which MBE is used in semiconductor manufacture. CVD may also make possible doping during CNT growth.

The dopant atoms are preferably non-carbon elements of the main group metals. The main group metals were discussed above. Typically, the dopant atoms are selected from the first row of the main group elements, and preferably includes, for example, boron (B), nitrogen (N), and oxygen (O).

The dopant atoms on the nanoscopic electrodes are selected based on chemical similarity to non-C,H atoms found in the molecule being studied. Preferably, the atoms are chemically similar by sharing characteristics of the valence shell, for example, by belonging to the same group of the Periodic Table. However, chemically similar atoms are not limited to the same chemical group, and can be, for example, neighboring atoms of the Periodic Table (e.g., oxygen neighbors with nitrogen, and therefore, it can be said that these atoms are also chemically similar).

From the above, it is evident that guanine, which contains both N and O non-C,H atoms, would more preferably be studied using N or O dopant atoms rather than P or S dopant atoms. Based on theoretical considerations alone, there would be no preference for choosing N over O, or O over N, in the case of guanine. As another example, in studying a phosphorylated adenine (e.g., adenosine triphosphate, ATP), a nitrogen, oxygen, or phosphorus dopant atom are all equally valid, based solely on theoretical considerations, since these atom types are all present in ATP. However, though there may not be a preference based on theoretical considerations, it necessarily remains possible that one dopant atom among different dopant atoms can show a preferred effect or superior result under different conditions, and hence, be preferred in a particular application over another dopant atom, even though the molecule being studied contains each dopant atom type.

In a preferred embodiment, at least one of the dopant atoms is equivalent to one of the non-C,H atoms in the molecule. For example, when selecting proper dopant atoms for studying an adenine base, the dopant atoms are most preferably nitrogen since nitrogen is the only non-C,H atom present in adenine. As another example, if an organothiol or organophosphine were being studied, it would be preferable for the dopant atom to be, respectively, sulfur and phosphorus.

In one embodiment, one or more dopant atoms are attached as pendant functional groups. For example, a nitrogen dopant atom can be covalently attached to a carbon nanotube as an amine (—NH$_2$), methylamine (—NHCH$_3$), amido (—C(O)NH$_2$), or nitro group (—NO$_2$); or an oxygen atom can be bound, for example, as a hydroxyl (—OH), peroxyl (—OOH), or carboxyl group (—COOH). In another embodiment, one or more dopant atoms are not pendant, but rather, occupy a space within the surface lattice structure of the nanoscopic electrode material. For example, nitrogen atoms may be incorporated into the $sp^2$-hybridized outer surface of a carbon nanotube as —N=N— groups. Incorporating nitrogen dopant atoms in this way may be advantageous in that disruption of the carbon nanotube lattice is minimized or eliminated. In this way, the conductivity of the nanotube is not diminished by a disruption of $sp^2$-promoted conduction.

In the case of nanotubes, the dopant atoms are preferably not only on the outer surface but at the terminal ends (i.e., crowns or endcaps) of the carbon nanotubes. Having the dopant atoms on the terminal ends generally makes the dopant atoms more accessible for interacting with the bridging molecule and the nanosized gap.

The nanoscopic electrodes are positioned so that dopant atoms residing thereon are within close enough proximity to the nanosized gap (i.e., are atomically close enough to the nanosized gap) to permit conduction by a tunneling mechanism that includes a resonant tunneling component. An example of a tunneling mechanism that includes a resonant tunneling component is a quasi-resonant tunneling mechanism. The exact position of the dopant atoms, and most of all the nature of the chemical bond with the electrode, are important parameters in providing the enhancement in molecular conductance.

In order for an apparatus to function for achieving the method described above, the nanoscopic electrodes described above are simultaneously connected to a power source and electrically interconnected with each other. The power source should be capable of applying a voltage bias of a magnitude that can generate current transmission though a bridging molecule in the nanogap in the absence of destructive or disabling effects on the bridging molecule or nanoscopic electrodes.

Typically, the nanoscopic electrodes are connected to the power source by electrical conductors that are in turn attached to the nanoscopic electrodes by metallic electrodes. In this way, the transverse tunneling current is measured. The CNT electrodes are attached to large electrode pads and the current that tunnels from one electrode through the molecule (e.g., DNA nucleotide) to the other electrode is measured. These are standard techniques used for measuring the transport properties of devices such as CNT FET or similar devices that have nanowires or nanoparticles as active elements.

The apparatus can further include any of the sensing elements or devices known in the art for sensing and/or measuring and/or transmitting an electronic characteristic of the bridging molecule when acted upon by a voltage bias provided at the electrodes.

The electrode system can be assembled using any of the techniques known in the art, such as the standard microelectronics processing techniques that can be modified for incorporation of CNTs. These techniques include lithography, dry or wet etching, and any other methods that can be controllably used for performing additive (growth and deposition) or subtractive (etching) processing. The method of processing is very much dependent on how the nanogap is to be created between the CNT electrodes.

Examples have been set forth below for the purpose of illustration and to describe the best mode of the invention at the present time. However, the scope of this invention is not to be in any way limited by the examples set forth herein.

EXAMPLE 1

Using density functional theory (DFT), it can be demonstrated that single-wall (metallic) CNTs, when properly terminated, can favorably replace metal electrodes, by enhancing the transverse electron transport across the DNA. In devices, nanotubes are connected to metallic electrodes attached to an external battery. Band realignment and charge injection in the vicinity of that "external" junction, as well as other imperfectness in the external circuitry have an effect on the magnitude of the direct current. However, nanotube leads are typically rather long (tens of nanometers) and screening takes place over a distance much shorter than the nanotube branch, supporting the assumption of the infinite leads. Therefore, this effect does not depend on the nanotube chemical ending close to the DNA nucleotide. The different behaviors for different endings will therefore be preserved (though the amplitude of the current might be modified). From a different perspective, it is noted that the effect of nanotube junction to external electrodes will not be expressed in a conventional four points measurement since it completely eliminates the effect of that type of contact.

To illustrate the enhancement of the conductivity with N doping, the electron transport for all four types of the DNA nucleotides (adenine (A), thymine (T), cytosine (C), and guanine (G)), with C-caped, and H and N nanotube terminations, was calculated in the geometry shown in FIG. 1. All the results correspond to the Landauer approach (see R. Landauer, Phil. Mag. 21, 863 (1970)), which establishes that the electron transmission probability, 1, is proportional to the molecular electronic conductance. T includes the detailed, quantum mechanical description of the molecule and its interaction with the leads. Assuming nearly thermodynamic equilibrium and a small voltage drop V across the system (from zero to 500 mV), the so-called linear-response, equilibrium regime is known to yield quantitative results compared to a full non-equilibrium approach where the Poisson's equation is solved self-consistently (see W. C. Lu, V. Meunier, and J. Bernholc, Phys. Rev. Lett. 95, 206805 (2005)). Within these assumptions, the electronic structure of the system is described according to self-consistent DFT calculations for the ground state. All-electron DFT calculations were performed using the quantum chemistry package NWChem (see R. A. Kendall et al., Comp. Phys. Comm. 128, 260 (2000)) with the 3-21 g contracted Gaussian basis set.

All of the results were verified using three different XC functional, i.e. with LDA (see S. H. Vosko, L. Wilk, and M. Nusair, Can. J. Phys. 58, 1200 (1980)), GGA (see J. P. Perdew, K. Burke, and M. Ernzerhof, Phys. Rev. Lett. 77, 3865 (1996)) and hybrid methods (B3LYP as shown in A. D. Becke, J. Chem. Phys. 98, 5648 (1993)), remarkably all leading to qualitatively the same conclusions. The numerical results shown herein correspond to the GGA functional, motivated by the fact that OGA is a good compromise for extended electronic systems and molecular systems.

For reasons discussed above, N-doped (5,5) nanotubes were used as preferred electrodes to measure increased currents through the DNA nucleotides in the nanogap (see FIG. 1 (c-f)). The subsystems contained a DNA nucleotide and a large part of the carbon nanotube (CNT) electrodes along with the appropriate terminations. To describe the open boundary conditions appropriate for the leads, the Green's function matching method can be used in conjunction with the generalized tight-binding (TB) approach to compute the transmission function T. See V. Meunier, and B. G. Sumpter, J. Chem. Phys. 123, 024705 (2005); P. S. Krstic, X. G. Zhang, and W. H. Butler, Phys. Rev. B 66, 205319 (2002); and M. Buongiomo Nardelli, Phys. Rev. B 60, 7828 (1999).

The integral of T(E,V) over the band energy E determines the current response I to the applied voltage V. The transmission function T depends on the electronic structure of the nucleotide but also on a number of other factors, e.g. the strength of the coupling between the base and the leads, which is a function of the base-lead geometry. Specifically, T is very sensitive to the energy matching of the asymptotic Bloch channels in the leads with the energy levels of the base, deformed (i.e. shifted and broadened) by the coupling with the leads and adapted to the chemical potential drop across the molecule, resulting from the applied bias. The approach takes all of these effects into account at the DFT level.

Figure 2:
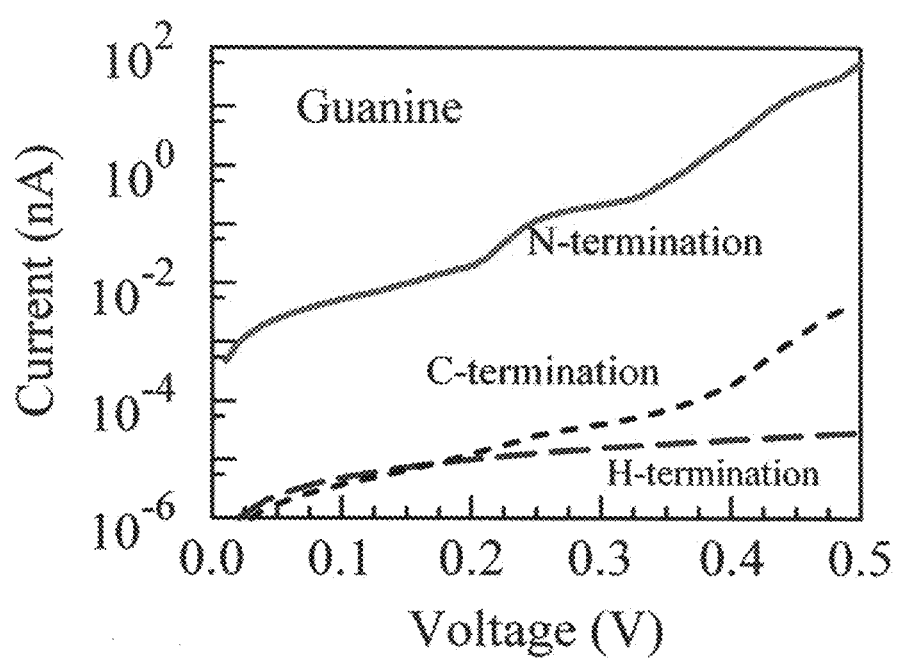
FIG. 2. Comparison of the I-V characteristics of guanine with N-, C- and H-terminated CNT leads.

Typical I-V characteristics for various lead terminations are illustrated with the example of guanine in FIG. 2. The current response for the N-terminated leads was found to be two to six orders of magnitude larger than that obtained with C- and H-terminations in the whole range of the considered biases. It is important to note that the current in the N-case reached nA values at about 0.4 V, while it stayed in sub-pA or pA range for C- and H-terminations, comparable to the values obtained using gold electrodes with similar electrode-nucleotide geometries.

Strong enhancement of the low-electric bias response with N-termination was found for all DNA nucleotides, as illustrated for two voltages in Table I. The enhancement factors also increased orders of magnitude with an increase of voltage from 0.1 to 0.5 V. All nucleotides showed an enhancement factor to the H-terminated leads, IN/IH, ranging between 105 and 106 for higher of the considered voltages. This factor to the C-termination, IN/IC, is more varying, between 107 for adenine, down to 103 for guanine.

| Bias (V) | A | G | C | T |
|---|---|---|---|---|
| IN/TC 0.1 | 6.3(3) | 1.4(3) | 7.0(1) | 5.6(3) |
| 0.5 | 1.1(7) | 8.8(3) | 4.1(4) | 2.8(6) |
| IN/IH 0.1 | 1.8(2) | 1.1(3) | 6.1(2) | 1.2(4) |
| 0.5 | 2.0(5) | 1.3(6) | 2.7(5) | 5.5(6) |

Table I: Current enhancements for various CNT terminations and for four DNA nucleotide types, with 0.1 and 0.5 V transverse biases. The format a(b) means a10b.

While the leads define the boundary conditions and supply the electrons at the Fermi energy EF, the physical mechanisms of transport across the inter-leads gap mainly depend upon the electronic structure of the molecule placed in the gap, while its coupling to the leads defines the tunneling characteristics of the junction. The existence of the electronic states localized in the gap, energetically close to the Fermi energy is of a decisive importance for the overall conductance. In the absence of such states, the mechanism of electron transport is dominated at low biases by the non-resonant tunneling, causing a significant suppression of conductance.

Figure 3:
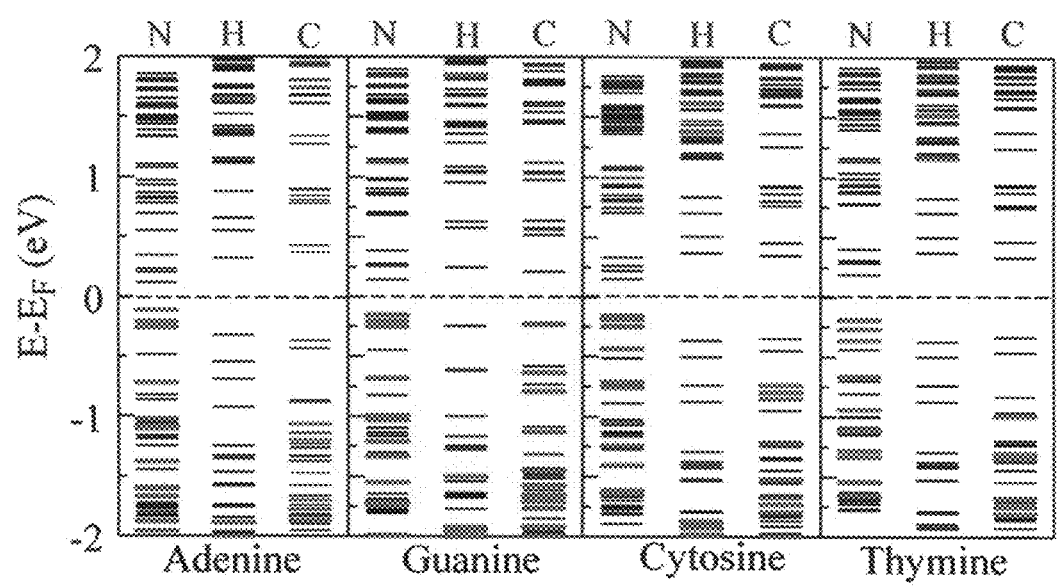
FIG. 3. (color) Spectra of eigen-energies of the extended molecule for various CNT terminations and various nucleotides. Black thin lines are orbitals located at the CNT leads while red-colored thick lines represent the orbitals located at DNA nucleotides. The Fermi energy is set to zero (dashed horizontal line) in each case.

FIG. 3 shows the eigen-energy spectra of the extended molecules of FIG. 1. The strong presence of states located mainly at nitrogen and oxygen atoms of a nucleotide, extending across the gap, is obvious for N-terminated leads, for all of the nucleotides. The fact that no such states are present close to EF in the case of the carbon and hydrogen terminations explains the large increase of current in nitrogen terminated CNTs.

The results can be further analyzed in terms of the improved coupling between the N-saturated edges of the nanotube with the heterocyclic compounds present at one end of each nucleotide since they share chemical similarity. DNA bases can be classified into two types: adenine and guanine are fused five- and six-membered heterocyclic compounds called purines, while cytosine and thymine are six-membered rings called pyrimidines. In the nanogap geometries used in the present work, G and A nucleotides share similar current profiles. This property is compatible with the chemical nature of the base. It follows that for all terminations these two molecules carry the largest transport current. C and T nucleotides yield a quite smaller current response. Again, this can be understood from the fact that C and T are pyrimidines compounds, i.e. they have a single nitrogen-carbon heterocyclic group which can account for a lower coupling than in the case of purine bases. The N-terminated CNT could, by its ability to distinguish between these bases, be an effective sensor for the (A,G) and (C,T) groups of the DNA bases. This ability to distinguish between similar types of molecules could be used for identifying or distinguishing between different types of molecules. For example, the method may be used to identify or distinguish between other types of biomolecules, such as amino acid-containing molecules, carbohydrates, sugars, lipids, and their conjugated forms.

The above examples show that the presence of N establishes a natural connection with purine and pyrimidines groups. Remarkably, the obtained selective enhancement of the current response, following from transition from regime of nonresonant to the quasi-resonant tunneling is not only limited to the DNA-related molecules. The local chemistry at the tip of the electrodes has a dramatic effect on the coupling with the molecule and functionalizing CNT ends offer interesting possibilities for molecular recognition using CNTs.

While there has been shown and described what are at present considered the preferred embodiments of the invention, it will be obvious to those skilled in the art that various changes and modifications can be prepared therein without departing from the scope of the inventions defined by the appended claims.

What is claimed is:

1. A nanoscopic electrode system for measuring the electron transport properties of a single molecule of interest, the nanoscopic electrode system comprising at least two electrically interconnected electrically conductive nanoscopic electrodes separated by a nanosized gap suitably miniscule so as to permit transmission of current by a tunneling mechanism while large enough to accommodate the molecule of interest, the nanoscopic electrodes being outer-surface functionalized by one or more non-C,H main group dopant atoms residing in a location of the nanoscopic electrode at the nanosized gap, wherein the one or more non-C,H main group dopant atoms are not pendant and occupy a space within a lattice of the nanoscopic electrode surface.

2. The nanoscopic electrode system according to claim 1, wherein the one or more non-C,H main group dopant atoms are one or a combination of atoms selected from nitrogen, boron, oxygen, phosphorus, and sulfur atoms.

3. The nanoscopic electrode system according to claim 1, wherein the one or more non-C,H main group dopant atoms are one or more nitrogen atoms.

4. The nanoscopic electrode system according to claim 1, wherein the nanoscopic electrodes are connected to a power source capable of applying a voltage bias of a magnitude that can generate current transmission through the bridging molecule in the absence of destructive or disabling effects on the bridging molecule or nanoscopic electrodes.

5. The nanoscopic electrode system according to claim 4, wherein the nanoscopic electrodes are connected to the power source by electrical conductors that are attached to the nanoscopic electrodes by metallic electrodes.

6. The nanoscopic electrode system according to claim 1, wherein the nanoscopic electrodes are carbon nanotubes.

7. The nanoscopic electrode system according to claim 6, wherein the carbon nanotubes are single-walled carbon nanotubes.

8. The nanoscopic electrode system according to claim 7, wherein the single-walled carbon nanotubes are outer-surface functionalized by one or more dopant atoms selected from nitrogen and oxygen dopant atoms.

9. The nanoscopic electrode system according to claim 6, wherein dopant atoms in the carbon nanotubes are located at one or more terminal end regions of the carbon nanotube.

10. The nanoscopic electrode system according to claim 1, wherein the electrode system further comprises sensing elements capable of sensing or measuring an electrical conducting characteristic of the bridging molecule.

11. The nanoscopic electrode system according to claim 1, wherein said nanoscopic electrodes are connected to macroscopic electrode pads.

12. The nanoscopic electrode system according to claim 1, wherein said nanoscopic electrodes are connected to macroscopic electrode pads.

13. A method for measuring an electron-transport property of a single molecule of interest, the method comprising:
(i) positioning a molecule of interest within a nanosized gap separating at least two electrically conductive nanoscopic electrodes in such a manner that the molecule of interest bridges and interacts with the nanoscopic electrodes, wherein the nanosized gap is suitably miniscule so as to permit transmission of current through the molecule of interest by a tunneling mechanism while large enough to accommodate the molecule of interest;
(ii) applying a voltage bias to the nanoscopic electrodes, the voltage bias being of a suitable magnitude so as to permit transmission of current by a tunneling mechanism; and
(iii) measuring an electron transport property of the molecule of interest;
wherein the nanoscopic electrodes are outer-surface functionalized by one or more non-C,H main group dopant atoms residing at the nanosized gap, wherein said non-C,H main group dopant atoms are selected so as to cause a non-covalent interaction between the non-C,H main group dopant atoms and said molecule of interest, and wherein application of a voltage bias to the nanoscopic electrodes results in conduction by a tunneling mechanism from said non-C,H main group dopant atom through said molecule of interest, wherein the molecule of interest interacts with dopant atoms of the nanoscopic electrodes by a non-covalent interaction to permit the molecule of interest to reversibly interact with the nanoscopic electrodes.

14. The method according to claim 13, wherein the one or more non-C,H main group dopant atoms are one or a combination of atoms selected from nitrogen, boron, oxygen, phosphorus, and sulfur atoms.

15. The method according to claim 14, wherein the one or more non-C,H main group dopant atoms are not pendant and occupy a space within a lattice of the nanoscopic electrode surface.

16. The method to claim 13, wherein the one or more non-C,H main group dopant atoms are selected from one or more dopant atoms selected from nitrogen and oxygen atoms.

17. The method according to claim 13, wherein the electron transport property being measured is electrical conductance.

18. The method according to claim 13, wherein the nanoscopic electrodes are carbon nanotubes.

19. The method according to claim 18, wherein the carbon nanotubes are single-walled carbon nanotubes.

20. The method according to claim 19, wherein the single-walled carbon nanotubes are outer-surface functionalized by one or more nitrogen dopant atoms.

21. The method according to claim 20, wherein said one or more nitrogen dopant atoms are not pendant and occupy a space within a lattice of the single-walled carbon nanotubes.

22. The method according to claim 18, wherein dopant atoms in the carbon nanotubes are located at one or more terminal end regions of the carbon nanotube.

23. The method according to claim 13, wherein the tunneling mechanism is a quasi-resonant tunneling mechanism.

24. The method according to claim 13, wherein the method further comprises employing sensing elements capable of sensing an electronic characteristic of the molecule of interest during application of the voltage bias.

25. The method according to claim 13, further comprising identifying a molecule or distinguishing one molecule from another by analysis of the electron-transport property measured.

26. The method according to claim 25, wherein the electron-transport property is electrical conductance, wherein a value of observed electrical conductance permits identification of a molecule, or a difference in observed electrical conductance between different molecules permits an identification of one or more molecules or an ability to distinguish the different molecules.

27. The method according to claim 13, wherein the molecule of interest is a biomolecule.

28. The method according to claim 27, wherein the biomolecule is a nucleobase-containing molecule, and wherein the nanoscopic electrodes have been doped with one or more dopant atoms selected from nitrogen and oxygen atoms.

29. The method according to claim 28, wherein the nucleobase-containing molecule is selected from nucleobase, nucleoside, nucleotide, oligonucleotide, and nucleic acid polymer.

30. The method according to claim 28, wherein one nucleobase-containing molecule is distinguished from another nucleobase-containing molecule by a difference in the electron-transport property measured for each nucleobase-containing molecule.

31. The method according to claim 27, wherein the biomolecule is an amino acid-containing molecule, and wherein the nanoscopic electrodes have been doped with one or more dopant atoms selected from nitrogen and oxygen atoms.

32. The method according to claim 31, wherein the amino acid-containing molecule is selected from amino acid, peptide, oligopeptide, and protein.

33. The method according to claim 31, wherein one amino acid-containing molecule is distinguished from another amino acid-containing molecule by a difference in the electron-transport property measured for each amino acid-containing molecule.

34. The method according to claim 13, wherein said tunneling mechanism includes a resonant tunneling component.

35. The method according to claim 13, wherein said non-covalent interaction is comprised of a hydrogen bonding interaction.

36. The method according to claim 13, wherein said positioning of said single molecule is achieved by a single-molecule manipulation technique.

37. The method according to claim 36, wherein said single-molecule manipulation technique comprises electrophoresis or dielectrophoresis.

38. The method according to claim 13, wherein, after an electron transport property of said molecule of interest is measured, said molecule is replaced by a different molecule and the electron transport property of said different molecule of interest is measured on the same nanoscopic electrode, or the electron transport property of a different portion of the same molecule of interest is measured on the same nanoscopic electrode.

39. The method according to claim 38, further comprising moving a strand of DNA through the nanogap to measure the electron transport properties of different portions of the DNA.

40. A method for producing a nanoscopic electrode system that enhances measurement of an electron transport property of a single molecule when the molecule is positioned between terminal ends of nanoscopic electrodes to which a low voltage bias is applied, the method comprising: functionalizing an outer surface of the terminal ends of said nanoscopic electrodes with non-C,H main group dopant atoms that will form a non-covalent interaction with said molecule, electrically interconnecting the functionalized nanoscopic electrodes, and arranging the functionalized nanoscopic electrodes to include a nanosized gap between said terminal ends to accommodate said molecule.

41. The method according to claim 40, wherein the molecule is a nucleobase-containing molecule.

42. A method for enhancing an electron transport property measurement of a molecule being studied when the molecule is positioned between terminal ends of nanoscopic electrodes to which a low voltage is applied, the method comprising: functionalizing an outer surface of the terminal ends of said nanoscopic electrodes with non-C,H main group dopant atoms that will form a non-covalent interaction with said molecule, electrically interconnecting the functionalized nanoscopic electrodes, arranging the functionalized nanoscopic electrodes to include a nanosized gap between said terminal ends to accommodate said molecule, positioning said molecule in the nanosized gap to interact non-covalently with the terminal ends of said nanoscopic electrodes, and measuring the electron transport property of said molecule when the low voltage bias is applied between the nanoscopic electrodes.

43. The method according to claim 42, wherein the molecule is a nucleobase-containing molecule.

* * * * *